United States Patent [19]

Terai et al.

[11] 4,454,748
[45] Jun. 19, 1984

[54] APPARATUS FOR MEASURING THE CONTENT OF HYDROGEN DISSOLVED IN A MOLTEN METAL

[75] Inventors: Shiro Terai; Shiro Sato; Sakae Kato; Masaya Imai; Susumu Inumaru; Masahiro Yoshida, all of Nagoya, Japan

[73] Assignee: Sumitomo Light Metal Industries, Ltd., Tokyo, Japan

[21] Appl. No.: 426,138

[22] Filed: Sep. 28, 1982

[51] Int. Cl.$^3$ .............................................. G01N 27/18
[52] U.S. Cl. ........................................ 73/19; 73/27 R
[58] Field of Search ................... 73/19, 27 R; 422/94, 422/96, 98; 340/632, 633, 634; 55/158, 270

[56] References Cited

U.S. PATENT DOCUMENTS 1,981,172 11/1934 Harrison .............................. 73/27 R
2,861,450 11/1958 Ransley ..................................... 73/19

FOREIGN PATENT DOCUMENTS 684865 12/1952 United Kingdom ..................... 73/19

Primary Examiner—Stephen A. Kreitman
Attorney, Agent, or Firm—Browdy and Neimark

[57] ABSTRACT

An apparatus for measuring the content of hydrogen dissolved in a molten metal, comprising an immersion head immersed within a batch of the molten metal to bring an inert gas into contact with the molten metal, an inert gas circulating device connected to the immersion head and having gas passages cooperating with the immersion head to form a closed circulatory path for circulating the inert gas a plurality of times through the path to and from the immersion head. The apparatus further comprises a hydrogen gas content measuring device connected to the gas passage for measuring the hydrogen-content of the inert gas flowing through the gas passage, the measuring device comprising a first measuring cell connected to the gas passage and having therein an electric resistance wire exposed to the circulated inert gas containing the hydrogen picked up from the molten metal, and further comprising a second measuring cell filled with atmosphere whose thermal conductivity is substantially equal to that of the inert gas. The measuring device includes a housing block which has portions to define a vacuum chamber surrounding each of the measuring cells in order to thermally separate the cell from the atmosphere surrounding the measuring device. The vacuum chambers for both cells are connected to each other and to a vacuum source. The housing block may be a cylindrical member of metal connected to an evacuation pipe.

11 Claims, 5 Drawing Figures

APPARATUS FOR MEASURING THE CONTENT OF HYDROGEN DISSOLVED IN A MOLTEN METAL

BACKGROUND OF THE INVENTION

The present invention relates to an apparatus for measuring the content or concentration of hydrogen dissolved in a molten metal. More particularly, the invention is concerned with improvements in an apparatus for direct measurement of the dissolved hydrogen-content of liquid metals, more specifically, of molten aluminum or aluminum alloys.

It was known that a hydrogen dissolved in molten aluminum, aluminum alloy or other molten metals causes voids or pores to develop within a body or batch of such molten metals during a process of solidification thereof, which pores give rise to various sorts of drawbacks or defects of the end products. Although these defects due to the pores had not been considered a serious problem, there has been an increasing requirement in recent years that so-called "dehydrogenation" be performed, i.e., the hydrogen dissolved in a molten metal be removed, as an important step of a metal casting process. Such demand has been increased keeping pace with an increasing demand for high-quality products, for example, structural aluminum panelings with fine surface finish as with anodic oxidation. In the anodic oxidation of such panelings, developments of minute "blisters" on the surfaces of aluminum sheets during a hot-processing operation will induce defects in the form of pits on the surface-finished panelings thereby degrading the quality of the end products.

In general, the dehydrogenation step requires a considerable period of time but the dehydrogenation, if conducted for a period longer than required, will lead to an elevated cost of manufacture of the end products. In consideration of these facts, it has been deemed to be a common practice and recommended to measure the content or concentration of hydrogen dissolved in a molten metal and use the measurements to keep the length of dehydrogenation to a necessary minumum.

In light of the above requirement for minimizing the dehydrogenation time and the consequent requirement for reducing the time spent in measuring the hydrogen-content of the molten metal, it has been proposed to adopt the so-called "Telegas" process wherein the measurement is carried out by an apparatus as shown in the U.K. Pat. No. 684,865 and the U.S. Pat. No. 2,861,450, the disclosure of which is hereby incorporated by reference.

A hydrogen gas content measuring apparatus used to practice such "Telegas" process, namely, a "Telegas" apparatus is a system which is adapted such that nitrogen or other inert gas is brought into contact with the body of molten metal by feeding the inert gas through one of two bores in an immersion head immersed in the molten metal while the inert gas in the molten metal is collected by the other bore and recirculated, through a pump, a hydrogen content detector, so-called katharometer, and the immersion head, back into the body of molten metal, this circulation of the inert gas being repeated until the pressure of the hydrogen gas picked up from the molten metal by the inert gas is in equilibrium with the content of hydrogen dissolved in the molten metal. Then, the mixture gas containing the hydrogen gas thus obtained through repeated circulation of the inert gas is measured in thermal conductivity by measuring electrical resistance variations of one hot-wire type detecting element (electric resistance wire) disposed in one of two measuring cells provided on the previously indicated hydrogen content detector. In the meantime, the other measuring cell or comparator cell is regularly charged with atmosphere whose thermal conductivity is substantially equal to that of the inert gas (nitrogen in this specific embodiment) flowing in said one measuring cell, whereby the electrical resistance of another hot-wire type detecting element is kept at a fixed value which is used as a reference with which the electrical resistance of said one detecting element is compared by an electric bridge circuit or network. More specifically, the difference between the two resistance values is used to obtain variations in thermal conductivity of the inert gas corresponding to the magnitude of partial pressure of the hydrogen in the circulated inert gas surrounding said one detecting element. In other words, the electric bridge circuit uses the electrical resistance differential value to obtain an out-of-balance current representing the magnitude of the equilibrium pressure of molecular hydrogen. This out-of-balance current is converted into a value of hydrogen gas content with reference to a calibration curve which represents a relationship between out-of-balance current values predetermined according to temperature of the molten metal, and hydrogen gas content values. The obtained value of hydrogen gas content is multiplied by a compensation constant selected depending upon specific metals in order to obtain a target value of the content of hydrogen dissolved in the molten metal.

Although the above conventional Telegas apparatus is capable of measuring directly the content of hydrogen (concentration of hydrogen gas) dissolved in a molten metal in a shorter period of time than with other methods wherein the concentration of hydrogen gas is measured by using a sample of solidified metals in question, such Telegas apparatus has not been considered completely satisfactory in operating efficiency for the reasons stated below.

The Telegas apparatus in the art uses a hydrogen content detector whose measuring cells are accommodated directly in bores formed in a housing block of brass or other similar metals. In such structure, a considerably long period of time is required before a thermal equilibrium has been reached among two hot-wire type detector elements of an electrical bridge network, metal block accommodating those elements, and a atmosphere surrounding the metal block. As a result, a comparatively long period of time is required before the reading of an ammeter connected to the bridge network has been stabilized so that the content of hydrogen in the molten metal is obtained.

The Telegas apparatus is also disadvantageous in that variations in temperature of the atmosphere surrounding the metal block will break the thermal equilibrium of the metal block with the hot-wire-type detector elements received within that block, thereby causing gradual variation in reading of the ammeter connected to the bridge network. This phenomenon not only requires an appreciable length of time to ensure that the ammeter reading has been restored to a steady value, but also requires re-calibration or zero-adjustment of the ammeter each time the thermal equilibrium is lost due to temperature variation of the atmosphere.

SUMMARY OF THE INVENTION

The present invention was made in view of the above background. Accordingly, it is an object of the invention to provide an improved apparatus for measuring the hydrogen content of molten metals, which assures less measuring time, high resistance or immunity to temperature variation of the surrounding atmosphere, and consequently minimum variation of the indicator reading, and reduced requirement for recalibration of the measuring device.

To attain the above object, an apparatus for measuring the content of hydrogen dissolved in a molten metal according to the invention comprises:

an immersion head immersed within a batch of the molten metal and having means for bringing an inert gas into contact with the molten metal;

circulatory means, connected to the immersion head and having a gas passage cooperating with the immersion head to constitute a closed path, for circulating the inert gas a plurality of times through the gas passage to and from the immersion head; and detecting means for determining the hydrogen-content of the inert gas flowing through the gas passage;

the detecting means comprising a first measuring cell connected to the gas passage and having therein an electric resistance wire exposed to the circulated inert gas containing the hydrogen, and a second measuring cell filled with atmosphere whose thermal conductivity is substantially equal to that of the inert gas, the second measuring cell having therein another electric resistance wire, the detecting means further comprising means for defining a vacuum space surrounding each of the first and second measuring cells.

In the apparatus according to the invention, the provision of first and second vacuum spaces or chambers surrounding the respective measuring cells accommodating the electric resistance wires which are respectively exposed to the hydrogen-containing inert gas and to the atmosphere or inert gas having substantially the same thermal conductivity as the hydrogen-containing inert gas, will effectively reduce thermal capacity of the cells as well as achieve thermal separation of the cells from the atmosphere surrounding the detecting means, whereby the measuring cells are not substantially affected by temperature variations of the surrounding atmosphere and is therefore able to become steady in temperature within a short time. Thus, the apparatus of this invention requires virtually no re-calibration or zero-adjustment of the measuring device and permits a significant reduction in the measuring time, which results in improved operating efficiency and reduced manufacturing cost of the products obtained.

These and other objects and features of the present invention will become apparent from the following description taken in connection with the accompanying drawings.

BRIEF DESCRIPTION OF THE DRAWINGS

The present invention is illustrated in the accompanying drawings in which.

DETAILED DESCRIPTION OF THE PREFERRED EMBODIMENTS

In order that the present invention may be more clearly understood, some embodiments thereof will now be described in detail by way of example with reference to the accompanying drawings.

Figure 1:
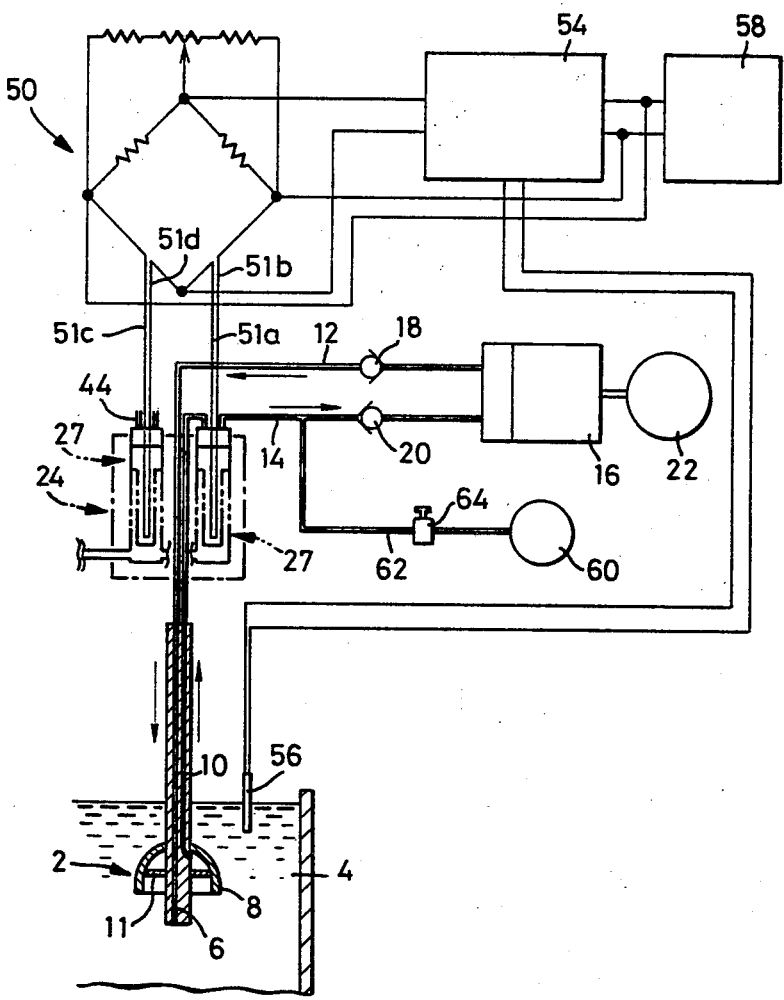
FIG. 1 is a schematic view of an embodiment of an apparatus of the present invention for measuring hydrogen content dissolved in a molten metal.

Referring first to FIG. 1 which presents a schematic view of one embodiment of an apparatus of the invention for measuring hydrogen content, there is shown a twin-bore probe (immersion head) 2 which is immersed within a batch of molten metal 4 such as molten aluminum or aluminum alloys. The twin-bore probe 2 comprises: a first bore 6 extending deeply into the batch of molten metal 4; a skirt 8 located above the immersed end of the first bore 6 and adapted to collect bubbles of nitrogen, argon or other inert gas ejected from the first bore 6; a second bore 10 which opens into the upper part of a space formed within the skirt 8; and a partition filter 11 of ceramic materials impervious to the molten metal and separating the upper part of the space within the skirt 8 from the lower part thereof, which partition filter 11 removes the molten metal from the inert gas bubbles admitted into the second bore 10. The bores 6 and 10 of the twin-bore probe 2 which are connected to a diaphragm pump 16 via tubes 12 and 14, respectively, cooperate with circulatory means including the diaphragm pump 16 and the tubes 12, 14, and with the molten metal 4, to constitute a closed path for circulatory flow of the inert gas.

More particularly stated, the tubes 12 and 14 include check valves 18 and 20 respectively which control a direction of flow of the inert gas in the closed path such that the inert gas is ejected from the first bore 6 of the twin-bore probe 2 into the molten metal 4. The inert gas is circulated repeatedly in that direction through the closed path by the actuation of the diaphragm pump 16 which is driven by a drive motor 22.

During the circulation in the closed path, the inert gas ejected into the molten metal 4 from the first bore 6 of the probe 2 reaches the skirt 8 in the form of bubbles flowing through the molten metal 4. In the meantime, the hydrogen dissolved in the molten metal 4 diffuses into the above stated bubbles during the repeated circulation of the inert gas through the closed path, and the partial pressure of the hydrogen contained in the inert gas bubbles gradually increases until it is finally in equilibrium with the content of the hydrogen dissolved in the molten metal 4. It is noted here that the hydrogen will not diffuse into the inert gas once the equilibrium pressure is reached.

Since the inert gas containing the hydrogen gas will have increasing thermal conductivity as the hydrogen gas contained therein is increased, the magnitude of the thermal conductivity of the inert gas is measured, when the hydrogen gas has reached its equilibrium pressure, by a hydrogen content detector 24 connected to the tube 14.

Figure 2:
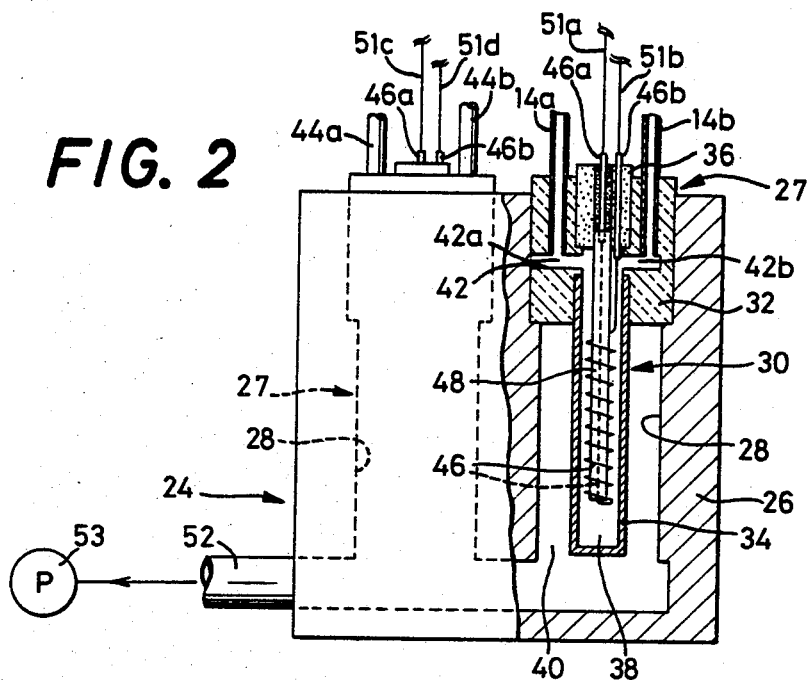
FIG. 2 is a cross sectional view showing essential parts of one form of a hydrogen content detector used in the apparatus of FIG. 1.

The hydrogen content detector 24, so-called katharometer, which is shown in FIG. 2 by way of example, comprises a housing block 26 of aluminum, brass or similar materials wherein there are provided a pair of detecting portions or units 27 for measuring thermal conductivity of the hydrogen-containing inert gas and of the atmosphere, respectively. Each of the detecting portions 27 includes a cylinder 28 formed in the housing block 26, and a measuring cell 30 which is accommodated in the cylinder 28, whereby the detecting portion 27 is formed of a double-cylinder structure.

As shown in FIG. 2, the cylinders 28 are each gas-tightly plugged with a cylindrical first sealing member 32 of heat insulating material which has an opening therein. Each of the measuring cells 30 includes a cylindrical vessel 34 of stainless or other metallic material, the open end portion of which is inserted in and adhered to the lower portion of the opening of the sealing member 32. In the upper portion of the opening of the first sealing member 32 is inserted gas-tightly a second sealing member 36 also of heat insulating material. Thus, the first sealing member 32 fitted in the open end portion of the cylinder 28 is adapted to form a gas diffusion chamber 38 within the vessel 34 and a vacuum chamber 40 outside of the vessel 34.

The gas diffusion chamber 38 of the first detecting portion 27 is connected, through passages 42 (42a, 42b) formed within the first sealing member 32, to tubes 14 (14a, 14b) which serve as passages for providing a flow of hydrogen-containing inert gas to and from the chamber 38. Stated in more detail, the inert gas flowing through the tube 14a is admitted through the passage 42a into the upper part of the gas diffusion chamber 38 while the inert gas within the chamber 38 is discharged through the passage 42b into the other tube 14b. On the other hand, the gas diffusion chamber 38 of the other or second detecting portion 27 is kept in communication with the atmosphere through tubes 44 (44a, 44b) so that the second cell 30 is charged with air whose thermal conductivity is substantially equal to that of the inert gas within the first cell.

These two diffusion chambers 38, that is, measuring cells 30 each accommodate a hot-wire type detector element (electric resistance wire) 46 of platinum or other similar material which varies in temperature, i.e., in electrical resistance as the thermal conductivity of the gas diffused in the chamber is changed. Thus, the thermal conductivity values of the hydrogen-containing inert gas and the atmosphere are detected by measuring the electrical resistance values of the hot-wire type detector elements 46. In this connection, it is noted that as the pressure of hydrogen in the inert gas becomes higher, the thermal conductivity of the inert gas becomes higher, the hot-wire type detector element 46 is cooled and its electrical resistance is lowered to unbalance a bridge network discussed later, thereby increasing out-of-balance current across the bridge.

In the present embodiment, the hot-wire type detector elements 46 are each supported by a hollow pipe (supporter) 48 of alumina, ceramics or other non-conductive material which extends from the second sealing member 36 down into the cell vessel 34. The detector element 46 is bent at the lower end of the hollow pipe 48 into two halves, one half being inserted through the interior of the hollow pipe 48 and the other half being wound in a spiral manner on the outer periphery of the hollow pipe 48, both toward the upper end of the pipe 48 such that the ends of both halves are connected to platinum wire stems 46a, 46b which penetrate through the second sealing member 36. The platinum wire stems 46a, 46b are further connected to lead-out wires 51a, 51b (51c, 51d) from a Wheatstone bridge circuit or arrangement 50.

The electric resistance wires 46 which are thus retained on the support 48 in a spiral manner will not have chances of short-circuiting at its intermediate portion between different parts thereof, or contact or collision thereof with the wall of the measuring cells, or other troubles inviting damages thereof due to vibration of the measuring cells 30, thereby contributing to prolonged service life and reduced detecting or measuring error of the measuring cell 30.

The vacuum chambers 40 in the pair of detecting portions 27 are communicated with each other within the housing block 26 and connected through an evacuation pipe 52 to a vacuum pump 53 so that the chambers 40 are evacuated by actuation of the vacuum pump 53. The vacuum chambers 40 which have been evacuated may be maintained in vacuum by plugging the evacuation pipe 52 with pressure tight fasteners (not shown), brazing or other suitable means known in the art.

The values of thermal conductivity of the hydrogen-containing inert gas and the atmosphere (air) which are converted into electrical resistance values by the hydrogen content detector 24, are compared with each other by the Wheatstone bridge circuit 50 illustrated in FIG. 1, which circuit 50 produces an output in the form of out-of-balance current corresponding to the obtained difference between the two values of thermal conductivity (electrical resistance). This out-of-balance current is passed to an arithmetic circuit 54 connected to the Wheatstone bridge circuit 50. The arithmetic circuit 54 processes the input out-of-balance current according to the predetermined formula to calculate and display the content of hydrogen in the molten metal in question (dissolved hydrogen content). Numeral 56 designates a thermocouple which is immersed within the body of the molten metal 4 to provide the arithmetic circuit 54 with temperature data of the molten metal 4, and numeral 58 designates a constant-voltage (constant-current) power circuit which supplies a direct current to the arithmetic circuit 54 and to the bridge circuit 50.

Reference numeral 60 in FIG. 1 indicates an inert gas cylinder which is connected via a tube 62 to the tube 14 between the hydrogen content detector 24 and the check valve 24 in order to introduce a suitable inert gas, e.g., nitrogen gas, into the closed path. The supply of the inert gas from the cylinder 60 is controlled by a stop valve 64 provided part way through the tube 62.

To make a measurement of the hydrogen content of the molten metal 4 with the above constructed apparatus, the stop valve 64 is opened, after turning on the power circuit 58, to charge the closed path with the inert gas from the cylinder 60. Then, the twin-bore probe 2 is slowly and gently immersed into the body of the molten metal 4 and the stop valve 64 is closed to shut off the supply of the inert gas into the closed path. In the meantime, the thermocouple 56 is also immersed within the molten metal 4 and the indicator of the arithmetic circuit 54 is checked to ensure that the indicator reading is zero. Upon confirmation of the zeroed indicator, the motor 22 is turned on to actuate the diaphragm pump 16 so that the inert gas is circulated a plurality of times within the closed path until the indicator reading of the arithmetic circuit 54 has reached a steady value. This steady value finally obtained is the measurement.

As described above, the present embodiment of an apparatus of the invention is characterized in that the vacuum chamber 40 provided so as to surround the measuring cell 30 functions to thermally separate the cell vessel 34 from the outside air and that the thermal capacity of the cell vessel 34 itself is kept small, so that the measured values may be stabilized in a short time with a result of reduced time for the measurement of the hydrogen content.

Figure 3:
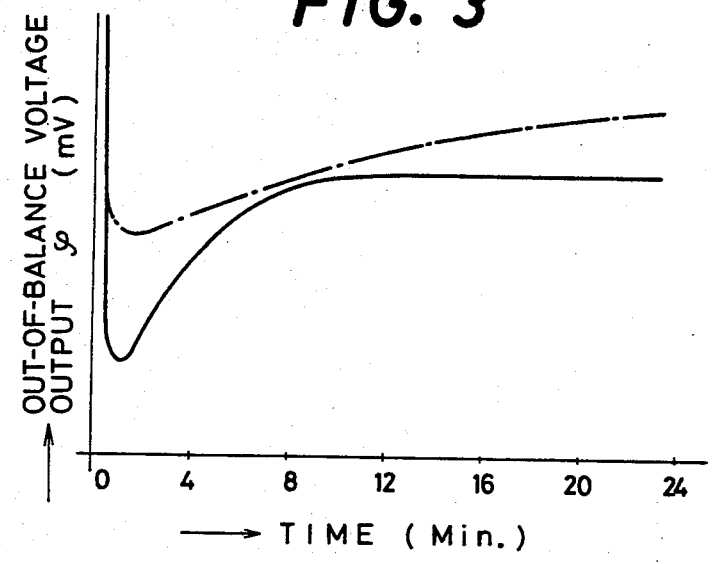
FIG. 3 is a graphical representation of out-of-balance voltage output ($\phi$) varying with time obtained in the measurment of hydrogen in a molten metal by the detector of FIG. 2, as compared with that by the conventional Telegas apparatus.

Referring next to FIG. 3, there are illustrated the results of experiments conducted by those including the inventors on the conventional Telegas apparatus and on the present hydrogen content measuring apparatus. The broken line indicates an out-of-balance voltage output $\phi$ (mV) varying with time obtained on the Telegas apparatus, and the solid line indicates the same on the present apparatus. As clearly shown in FIG. 3, the measurement or the indicator reading on the Telegas apparatus has not been stabilized even at a point of time 24 minutes after commencement of the measurement (after turning on the detector and a power switch of the associated power circuit) while, on the other hand, the indicator reading on the present apparatus has reached a steady value (which indicates the thermal equilibrium condition) in about 10 minutes after the commencement. Thus, the figure demonstrates that the time required for measuring the hydrogen content of a molten metal is extremely reduced on the present apparatus in comparison with that on the conventional apparatus.

The above out-of-balance voltage output is obtained or expressed by the following equation provided that heat radiation and convection are negligible:

$$\rho = \frac{1}{2} I \cdot Rf \cdot \frac{\alpha(t_f - t_c)}{1 + \alpha t_f} \cdot \delta \cdot \frac{\gamma}{1 + \gamma}$$

where,
I: Direct current supplied to the Wheatstone bridge circuit,
Rf: Electrical resistance of the electric resistance wire exposed to the hydrogen-containing inert gas,
$\alpha$: Temperature coefficient of the above electric resistance wire,
$t_f$: Temperature of the above electric resistance wire,
$t_c$: Temperature of inner wall surface of the measuring cell,
$\delta$: Ratio of thermal conductivity variation $\Delta\lambda$ (due to entry of hydrogen) to thermal conductivity $\lambda$ of the inert gas only, at an average temperature within the measuring cell,
$\gamma$: Ratio of electrical resistance R of the electric resistance wire exposed to the atmosphere to electrical resistance Rf, and
$R_r$: Input impedance of the recorder, and where the following relation is established:

$$2Rr >> Rf + R$$

Figure 4:
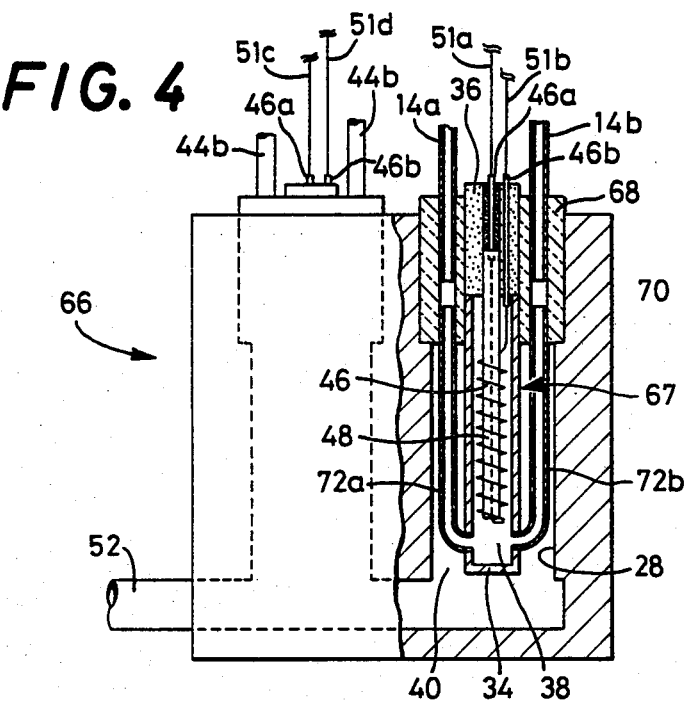
FIGS. 4 and 5 are cross sectional views showing essential parts of other forms of the hydrogen content detector used in the present apparatus.
Figure 5:
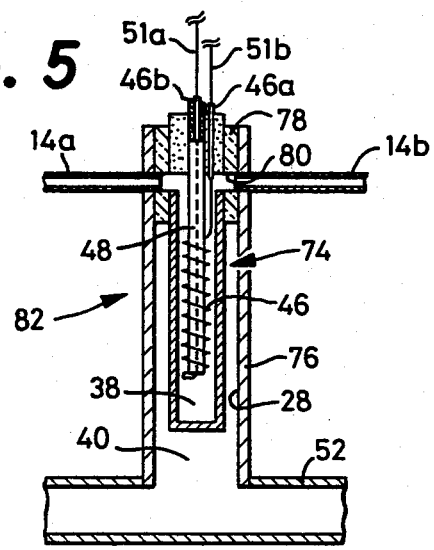

The hydrogen content detector 24 constructed as shown in FIG. 2 as an non-limiting example in the above embodiment may be modified as shown in FIGS. 4 and 5.

More specifically, measuring cells 67 of a hydrogen content detector 66 shown in FIG. 4 are each constructed such that the ends of the tubes 14a, 14b and tubes 72a, 72b are fixedly and gas-tightly inserted in passages 70 which are formed in a first sealing member 68 so as to otherwise communicate the interior of the cylinder 28 with the atmosphere and such that the ends of the tubes 72a, 72b remote from the inserted ends are connected to a lower end portion of the cell vessel 67 so that the inert gas admitted into the diffusion chamber 38 diffuses from the lower part of the chamber 38 toward the upper part thereof. Other parts of the detector 66 are identical to those of the previous embodiment and the detailed description thereof is omitted herein as the like parts are designated by the same reference numerals.

Measuring cells 74 shown in FIG. 5 are each accommodated in the cylinder 28 which is defined by an outer cylindrical structure formed of a metal tube 76 connected by welding to the evacuation pipe 52. The tubes 14a, 14b are each connected to an upper part of the diffusion chamber 38 such that the ends of the tubes 14a, 14b extend through openings formed in the peripheral wall of the metal tube 76 and through passages 80 formed in the first sealing member 78. The hollow pipe 48 is projected at its upper end into the atmosphere, but the inner opening is sealed gas-tightly with suitable sealing materials.

The hydrogen content detector 82 of FIG. 5 may be constructed compactly because the metal tube 76 is able to function as the cylinder 28, and effectively utilized when it is disposed within a thermostat.

While the foregoing description of the invention has been associated with the hydrogen content detectors of diffusion type in which the electric resistance wire is not located in the flow of the hydrogen-containing inert gas, the present invention may apply to detectors of semi-diffusion, or flow-through type in which the electric resistance wire is located in the flow of the hydrogen-containing inert gas.

It is understood that other modifications and variations of the measuring apparatus of the invention may be made without departing from the scope of the invention defined in the appended claims. For example, the arithmetic circuit 54 may be replaced by conventionally practiced manual calculation of the hydrogen content of a molten metal by conversion of the measured out-of-balance current with reference to a predetermined calibration curve. As another example, the motor 22 to drive the diaphragm pump 16 may be replaced by a valve mechanism for controlling the flow of the inert gas.

What is claimed is:

1. An apparatus for measuring the content of hydrogen dissolved in a molten metal, which comprises:
   an immersion head immersed within a batch of the molten metal and having means for bringing an inert gas into contact with the molten metal;
   circulatory means, connected to said immersion head and having a gas passage cooperating with said immersion head to constitute a closed path, for circulating the inert gas a plurality of times through said gas passage to and from said immersion head; and
   detecting means for determining the hydrogen-content of the inert gas flowing through said gas passage,
   said detecting means comprising a first measuring cell connected to said gas passage and having therein an electric resistance wire exposed to the circulated inert gas containing the hydrogen, and a second measuring cell filled with atmosphere whose thermal conductivity is substantially equal to that of said inert gas, said second measuring cell having therein another electric resistance wire, said detecting means further comprising means defining a vacuum space surrounding each of said first and second measuring cells.

2. An apparatus as set forth in claim 1, wherein said electric resistance wire is wound on a support member extending within said measuring cell.

3. An apparatus as set forth in claim 1 or 2, wherein said detecting means further comprises a housing block having bores accommodating said measuring cells respectively, said vacuum space being defined by an inner wall surface defining said bores and by the outer peripheral surface of said measuring cell, and connected to and evacuated by a vacuum source to maintain said vacuum space in vacuum.

4. An apparatus as set forth in claim 1, wherein said vacuum space surrounding said first measuring cell and said vacuum space surrounding said second measuring cell are communicated with each other.

5. An apparatus as set forth in claim 1 or 2, wherein said vacuum space is evacuated and maintained in vacuum with pressure-tight sealing means.

6. An apparatus as set forth in claim 1 or 2, wherein said detecting means further comprises means for defining outer cylindrical members radially outwardly of said measuring cells which act as inner cylindrical members, said outer and inner cylindrical members cooperating to form double-cylinder structures for accommodating said electric resistance wires respectively, said vacuum space being formed between said inner and outer cylindrical members.

7. An apparatus as set forth in claim 6, wherein said means for defining said outer cylindrical members comprises portions of a housing block having bores accommodating said measuring cells.

8. An apparatus as set forth in claim 6, wherein said means for defining said outer cylindrical members comprises metal tubings accommodating therein said measuring cells respectively, said metal tubings being each connected to a vacuum source to maintain said vacuum space in vacuum.

9. An apparatus as set forth in claim 1, wherein said atmosphere filled in the second measuring cell is air.

10. An apparatus as set forth in claim 1, wherein said atmosphere filled in the second measuring cell is an inert gas.

11. An apparatus as set forth in claim 1, wherein said molten metal is molten aluminum or aluminum alloy.

* * * * *